(12) United States Patent
Diasti et al.

(10) Patent No.: US 6,517,350 B2
(45) Date of Patent: Feb. 11, 2003

(54) METHOD FOR WHITENING TEETH (75) Inventors: Adam Diasti, Tampa, FL (US); Graham K. Philp, Jr., Palm Harbor, FL (US); Damon J. Brown, Tampa, FL (US)

(73) Assignee: Dentovations Inc., Tampa, FL (US)

( * ) Notice: Subject to any disclaimer, the term of this patent is extended or adjusted under 35 U.S.C. 154(b) by 11 days.

(21) Appl. No.: 09/797,855

(22) Filed: Mar. 5, 2001

(65) Prior Publication Data
US 2002/0004190 A1 Jan. 10, 2002

Related U.S. Application Data
(60) Provisional application No. 60/207,183, filed on May 26, 2000, and provisional application No. 60/213,297, filed on Jun. 22, 2000.

(51) Int. Cl.$^7$ .................................................. A61C 5/00
(52) U.S. Cl. .................. 433/215; 433/216; 424/49; 424/53
(58) Field of Search .............................. 433/215, 216; 424/49–88

(56) References Cited

U.S. PATENT DOCUMENTS

| 3,278,520 A | 10/1966 | Klug |
| 3,278,521 A | 10/1966 | Klug |
| 3,567,823 A | 3/1971 | Yamaga et al. |
| 4,556,561 A | 12/1985 | Brown et al. |
| 4,684,517 A | 8/1987 | Clipper et al. |
| 4,976,955 A | 12/1990 | Libin |
| 4,980,152 A | 12/1990 | Frazier et al. |
| 4,983,380 A | 1/1991 | Yarborough |
| 5,000,942 A | 3/1991 | Libin |
| 5,009,885 A | 4/1991 | Yarborough |
| 5,032,178 A | 7/1991 | Cornell |
| 5,084,268 A | 1/1992 | Thaler |
| 5,139,768 A | 8/1992 | Friedman |
| 5,171,564 A | 12/1992 | Nathoo et al. |
| 5,208,010 A | 5/1993 | Thaler |
| 5,217,710 A | 6/1993 | William et al. |
| 5,234,342 A * | 8/1993 | Fischer ........................ 433/215 |
| 5,264,205 A | 11/1993 | Kelly |
| 5,279,816 A | 1/1994 | Church et al. |
| 5,290,566 A | 3/1994 | Schow et al. |
| 5,302,375 A | 4/1994 | Viscio |
| 5,310,563 A | 5/1994 | Curtis et al. |
| 5,372,802 A | 12/1994 | Barrows et al. |
| 5,376,006 A | 12/1994 | Fischer |
| 5,395,241 A | 3/1995 | Kandelman |
| 5,403,577 A | 4/1995 | Friedman |
| 5,403,578 A | 4/1995 | Gordon |
| 5,409,631 A | 4/1995 | Fischer |
| 5,425,953 A | 6/1995 | Sintov et al. |
| 5,437,858 A | 8/1995 | Hungerbach et al. |
| 5,614,174 A | 3/1997 | Hsu et al. |
| 5,631,000 A | 5/1997 | Pellico et al. |
| 5,690,912 A | 11/1997 | Campbell et al. |
| 5,693,315 A | 12/1997 | Bevilacqua |
| 5,698,182 A | 12/1997 | Prencipe et al. |
| 5,708,052 A | 1/1998 | Fischer et al. |
| 5,718,886 A | 2/1998 | Pellico |
| 5,746,598 A | 5/1998 | Fischer |
| 5,766,574 A | 6/1998 | Christina-Beck et al. |

(List continued on next page.)

Primary Examiner—Nicholas D. Lucchesi
(74) Attorney, Agent, or Firm—Shlesinger, Arkwright & Garvey LLP (57) ABSTRACT

Tooth whitening compound includes a whitener and a carrier selected for adhering the carrier and whitening composition to a patient's teeth. The whitening compound may be applied in an uncovered layer. The whitening compound may be applied by the method including painting, washing, sponging, coating, daubing, spraying, wiping, rubbing, and by any movement relative to a horizontal or vertical axis of the patient's tooth. A whitening compound and method of applying such may be carried out with or without a coating covering the layer of whitening compound applied to the patient's teeth.

68 Claims, 2 Drawing Sheets

U.S. PATENT DOCUMENTS

| | | | |
|---|---|---|---|
| 5,780,015 | A | 7/1998 | Fisher et al. |
| 5,785,527 | A | 7/1998 | Jensen et al. |
| 5,785,957 | A | 7/1998 | Losee et al. |
| 5,792,446 | A | 8/1998 | Ashley |
| 5,797,749 | A | 8/1998 | Bertolotti et al. |
| 5,814,304 | A | 9/1998 | Wong et al. |
| 5,820,852 | A | 10/1998 | Burgess et al. |
| 5,824,289 | A | 10/1998 | Stoltz |
| 5,846,570 | A | 12/1998 | Barrow et al. |
| 5,849,266 | A | 12/1998 | Friedman |
| 5,849,269 | A | 12/1998 | Burgess et al. |
| 5,851,512 | A | 12/1998 | Fischer |
| 5,855,870 | A * | 1/1999 | Fischer .................. 433/215 X |
| 5,858,332 | A | 1/1999 | Jensen et al. |
| 5,879,691 | A | 3/1999 | Sagel et al. |
| 5,891,453 | A | 4/1999 | Sagel et al. |
| 5,902,568 | A | 5/1999 | Ryles et al. |
| 5,922,307 | A | 7/1999 | Montgomery |
| 5,928,628 | A | 7/1999 | Pellico |
| 5,985,249 | A | 11/1999 | Fischer |
| 6,030,222 | A | 2/2000 | Tarver |
| 6,036,493 | A | 3/2000 | Sharma |
| 6,183,251 | B1 | 2/2001 | Fischer |
| 6,312,666 | B1 * | 11/2001 | Oxman et al. .......... 433/215 X |
| 6,419,906 | B1 * | 7/2002 | Xu et al. ...................... 424/53 |

* cited by examiner

METHOD FOR WHITENING TEETH

CROSS REFERENCE TO RELATED APPLICATIONS

This application claims the priority of application Ser. No. 60/207,183, filed May 26, 2000, and this application claims the priority of application Ser. No. 60/213,297, filed Jun. 22, 2000, and each of which is incorporated herein by reference.

FIELD OF THE INVENTION

The invention relates to systems and methods for treating teeth. More specifically, the invention relates to a system (e.g., a novel delivery system) for delivering a tooth whitener to a tooth is and a method for whitening teeth. The invention likewise relates to a system and method for whitening teeth without the use of a mouth tray or other retaining device of the type which retain the tooth whitener in place against the teeth during use.

BACKGROUND OF THE INVENTION

Tooth whiteners are known. Conventional tooth whiteners are laborious, unwieldy, and expensive.

Conventional tooth whitening methods are complicated and expensive, and, hence, are limited to a small portion of the population.

In one typical method, the patient whose teeth are to be whitened must first visit a dentist in order to have a mouth tray made which is molded to fit that patient's teeth from a cast made from an impression.

After the conventional steps of producing the mouth tray have been completed, then the mouth tray is given to the patient, along with the tooth whitening compound(s).

In some tooth whitening methods, the patient then takes the tooth whitening compounds home, and uses them in conjunction with the mouth tray in the privacy of his or her home.

In use, the mouth tray is at least partially filled by the patient with the tooth whitening compound provided by the dental practitioner.

The patient must then take the proper mouth tray for the respective upper or lower jaw and press the mouth tray filled with whitening compound up (or down) against the teeth to be whitened.

The patient then holds the mouth tray filled with the compound in place against the teeth for a specified period of time.

After the specified period of time, the patient removes the mouth tray and the bulk of the compound, and discards the used whitening compound.

Typically, the whitening procedure is a multi-day procedure.

U.S. Pat. No. 5,879,691 to Sagel et al. discloses a delivery system for a tooth whitener using a strip of material having low flexural stiffness.

Some known conventional whitening methods (e.g., the type of methods that utilize either an traditional tray or an adhesive strip) require that the whitening compound be forced on the gingival tissue in the region adjacent to the teeth to be whitened. That forcing whitening compound on the gingival tissue may result in a burning sensation to that tissue.

Known prior art patents include:

| | |
|---|---|
| 5,693,315 | Bevilacqua |
| 5,780,015 | Fisher et al. |
| 5,792,446 | Ashley |
| 5,139,768 | Friedman |
| 3,567,823 | Yamaga et al. |
| 5,403,577 | Friedman |
| 5,690,912 | Campbell et al. |
| 5,849,266 | Friedman |
| 4,556,561 | Brown et al. |
| 5,395,241 | Kandelman |
| 5,797,749 | Bertolotti et al. |
| 5,032,178 | Cornell |
| 5,279,816 | Church et al. |
| 5,290,566 | Schow et al. |
| 5,302,375 | Viscio |
| 5,409,631 | Fischer |
| 5,425,953 | Sintov et al. |
| 5,631,000 | Pellico et al. |
| 5,698,182 | Prencipe et al. |
| 5,718,886 | Pellico |
| 5,746,598 | Fischer |
| 5,785,527 | Jensen et al. |
| 5,858,332 | Jensen et al. |
| 5,922,307 | Montgomery |
| 5,928,628 | Pellico |
| 6,030,222 | Tarver |
| 6,036,493 | Sharma |
| 4,976,955 | Libin |
| 5,000,942 | Libin |
| 5,264,205 | Kelly |
| 5,310,563 | Curtis et al. |
| 5,614,174 | Hsu et al. |
| 5,766,574 | Christina-Beck et al. |
| 5,785,957 | Losee et al. |
| 5,814,304 | Wong et al. |
| 5,879,691 | Sagel et al. |
| 5,891,453 | Sagel et al. |
| 5,902,568 | Ryles et al. |
| 5,084,268 | Thaler |
| 5,171,564 | Nathoo et al. |
| 5,208,010 | Thaler |
| 5,376,006 | Fischer |
| 5,437,858 | Hungerbach et al. |
| 5,846,570 | Barrow et al. |
| 5,985,249 | Fischer |
| 4,980,152 | Frazier et al. |
| 4,983,380 | Yarborough |
| 5,820,852 | Burgess et al. |
| 5,849,269 | Burgess et al. |
| 5,372,802 | Barrows et al. |
| 5,403,578 | Gordon |
| 4,684,517 | Clipper et al. |
| 5,009,885 | Yarborough |
| 5,217,710 | Williams et al. |
| 5,851,512 | Fischer |
| 5,708,052 | Fischer et al. |
| 5,824,289 | Stoltz |
| 6,183,251 | Fischer |

Many known whitening compounds have the drawback that they dry out the teeth, in use, owing to the whitening compounds drawing moisture out of the teeth. Such dried out teeth are more sensitive to hot and cold. Accordingly, many prior art whiteners required desensitizers (desensitizing compounds) so that the patients would not be bothered by their temperature-sensitive dried out teeth.

OBJECTS AND SUMMARY OF THE INVENTION

It is an object of the invention to overcome the drawbacks of the prior art methods, compounds, and devices.

A further object of the invention is to provide a tooth whitening method that is easier to use, more cost effective, and available to a greater percentage of the population.

A still further object of the invention is to provide a tooth whitening method that eliminates the need for mouth trays which fit the respective upper and lower sets of teeth in the patient's mouth for retaining the whitening compound against the teeth to be whitened, as in the conventional methods.

Yet another object of the invention is to eliminate entirely the need for a mouth tray to retain the tooth whitening compound.

Yet another object of the invention is to provide a tooth whitening method which is easier to use than the known methods.

Another object of the invention is to provide a tooth whitening system and method which dries out the user's teeth less than conventional whitening methods, so that the use of tooth desensitizing agents in the whitening compound may be reduced or eliminated.

A further object of the invention is to provide a tooth whitener system and method that directly applies a whitening agent onto the surfaces of the patient's teeth, thus eliminating the need for any type of tray or other mechanical retention device to retain the whitening agent on the surfaces of the teeth.

Another object of the invention is to provide a whitener delivery system which reduces or eliminates the discomfort or burning sensation of the patient's gingival tissue that may occur when using prior art delivery systems.

Yet another object of the invention is to provide a tooth whitening system in which the whitening compounds are applied substantially directly to the facial and labial surfaces of the teeth to be whitened.

Another object of the invention is to provide a tooth whitening system and method which reduce or eliminate the annoyance and inconvenience of using and wearing pre-made trays or adhesive-type products.

A still further object of the invention is to provide a tooth whitening system and method which are more effective than known over-the-counter whitening methods requiring the use of boil-and-bite type trays that do not fit the teeth properly and, hence, are often ineffective and result in less than desirable tooth whitening.

In summary, the invention provides a tooth whitening method which can be performed without the use of a mouth tray for retaining a tooth whitening compound against the patient's teeth.

It should be understood that relative terms such as up, and down are for convenience only and are not intended to be limiting.

It should likewise be understood that throughout the specification the features and advantages described in connection with the tooth whitening system apply equally to the features and advantages of the method of whitening teeth described herein.

Relative terms such as up, down, left, and right are for convenience only and are not intended to be limiting.

The term painting is intended to cover all manner of applying a layer of the whitening compound to a tooth, the term painting including, but not limited to brushing, sponging, coating, daubing, spraying, wiping, rubbing, and applying by movement relative to the tooth (i.e., any movement relative to a vertical or horizontal axis of a tooth) yielding a layer of whitening compound on the tooth. The movement relative to the tooth is not intended to be limited to movement toward and away from the gum. For example, spraying and daubing may be carried out with little or essentially no movement along an axis that is at an acute angle relative to the longitudinal axis of the tooth (e.g., a central, substantially vertical axis of a patient's tooth).

DETAILED DESCRIPTION OF THE INVENTION

Figure 1:
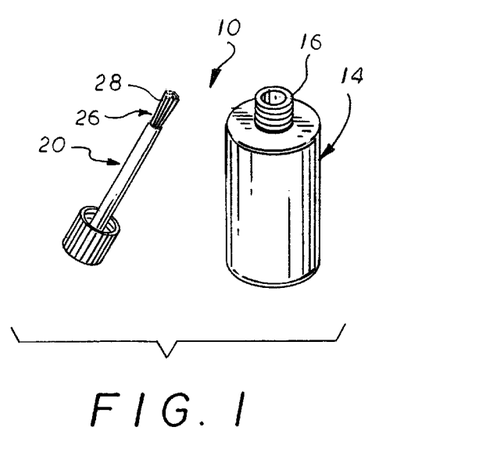
FIG. 1 is a elevational view of a tooth whitening system accordingly to the invention.
Figure 2:
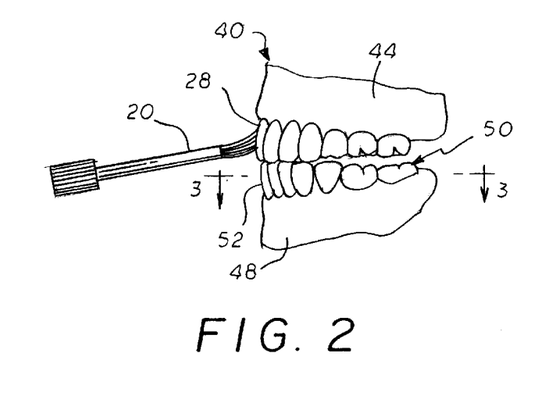
FIG. 2 shows the brush of FIG. 1 in use.
Figure 3:
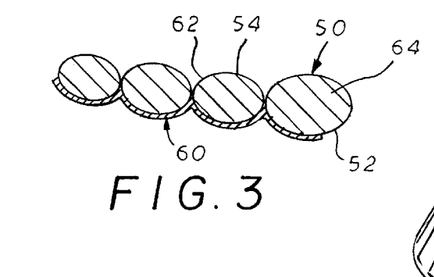
FIG. 3 shows a first layer or whitening agent as applied to the user's teeth, which is a cross sectional view of teeth taken along line 3—3 of FIG. 2.

FIGS. 1–3 illustrate a first preferred embodiment of a tooth whitening delivery system 10 according to a first preferred embodiment of the invention.

Tooth whitening system 10 includes a container 14 for holding a whitening agent or first whitening compound 60. Container 14 may be provided with a resealable opening 16 for repeated access to the inside and, hence, the contents of container 14.

A brush 20 having a handle 24 and bristles 26 may be provided for applying the whitening agent held in container 14.

Bristles 26 may have tips 28 configured for applying the whitening agent to the user's teeth.

Brush 20 may be disposable, or may take another form, as described below.

FIG. 2 illustrates the user's or patient's jaw 40 including an upper jaw 44 and a lower jaw 48.

Teeth 50 include an outer surface 52 and a corresponding inner surface 54.

In some cases, only outer surface 52 will be whitened by use of the whitening agent 60, as it is outer surface 52 which is visible when the user's lips are drawn back exposing teeth 50.

FIG. 2 illustrates how brush 20 is applying the whitening agent on outer surface 52 of teeth 50. It should be noted that bristles 28 may be configured and sized so as to reach all exposed surfaces of teeth 50. Preferably, brush 26 and bristles 28 are selected so that the whitening agent 60 may be applied directly to all the exposed surfaces which the patient desires to whiten.

A single coat or multiple coats or layers of whitening agent 60 may be applied.

Whitening agent 60 is formulated so that it need not be covered use by a device, such as a tray or tape, as the formulation is selected so that contact of whitening agent 60 with the mouth tissue causes little or no discomfort nor harm to the mouth tissue.

FIG. 3 illustrates the manner in which the whitening agent or the bristles 26 or both are selected so that whitening agent or first layer 60 extends into the exposed crevices 62 between teeth 64, for example. FIG. 3 shows whitening agent 62 applied to the outer surfaces 52 of tooth 64.

Whitening agent 60 of FIGS. 1–3 is formulated so as to require no covering protective layer, in use, unlike in the embodiment of FIGS. 4–6, as described below.

In other words, whitening agent 60 of FIGS. 1–3 has been successfully used with only first layer 60 as the whitening agent. In use, there was no apparent burning or ill effects of whitening agents 60 when whitening agent 60 contacted the mouth tissue.

However, there may be patients or applications for which a covering or protective layer of material is desired or useful. An embodiment in which a covering or protective layer is used in outlined below in connection with the embodiment of FIGS. 4–6.

Figure 4:
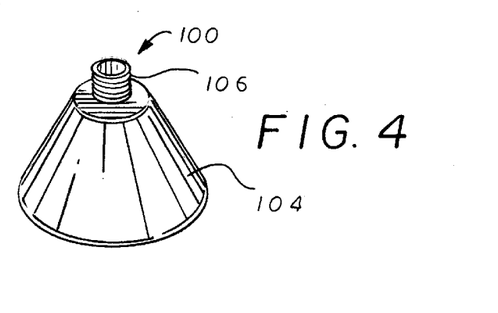
FIG. 4 illustrates a further container for use with a further preferred embodiment of a tooth whitening system according to the invention.
Figure 5:
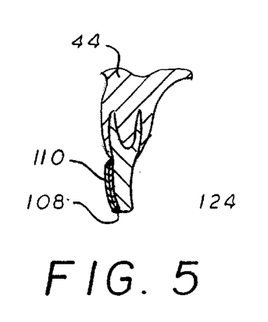
FIG. 5 is a cross sectional view of a user's incisor with a whitening layer and an overcoat layer on the front surface of the tooth.
Figure 6:
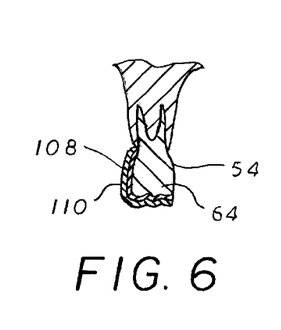
FIG. 6 illustrates a user's molar with a whitening layer covered by an overcoat layer, both of which are disposed on the front and lower face of the tooth.

FIGS. 4–6 illustrate another preferred embodiment of a whitening system 100 according to the invention. Whitening system 100 includes a container 104 having an opening 106 for providing access to the contents of container 104.

Container 104 may be provided with a second material which differs from the first material or whitening agent 108. The second material will be termed an overcoat to highlight the use of the second material.

The second material or overcoat or layer 110 may be applied on top of the first material or whitening agent 108. That is, the overcoat 110 may be applied to whitening agent 108 after whitening agent 108 has been applied to teeth 108.

Overcoat 108 may be a material selected so as to protect the soft tissue in the patient's mouth.

The use of overcoat 110 eliminates the need to protect the soft tissue of the patient's mouth by use of a mouth tray surrounding the whitening agent of prior art systems.

FIG. 5 illustrates how one of the patient's incisors 124 is whitened. In the case of incisor 124 the whitening agent 108 may be applied only to the outer surface 52 of incisor 124. Then, overcoat 110 is applied on top of whitening agent 108.

Typically, a user will find it unnecessary to whiten the inner surfaces 54 of his or her incisors 124, as the inner surfaces of the user's incisors 124 are rarely visible to others, for example.

FIG. 6 illustrates the case where a user would like to whiten the outer surface 52 as well as the lower surfaces of his or her teeth, such as the illustrated molars 64. In that case, whitening agent 108 is applied to outer surface 52 as well as the lower surface of the illustrated upper molar. Then, the overcoat 110 is applied to the whitening agent 108 so as to cover whitening agent 108 substantially completely, in most cases.

In the case where the user would like to whiten the inner surface 54 of molar 64, the whitening agent 108 and overcoat 110, in turn, will be applied to inner surface 54 of the molar.

Figure 7:
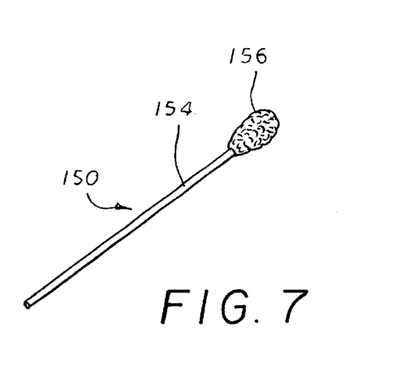
FIG. 7 shows a further preferred embodiment of an applicator for use with the systems according to the invention.

FIG. 7 illustrates another preferred embodiment of an applicator 150, according to the invention.

Applicator 150 includes a handle 154 and a material 156 disposed at one of its ends. The material may be a soft absorbent material such as cotton, and applicator 150 may take the form of a cotton swab.

Applicator 150 may be disposable. Applicator 150 may be a cotton swab such as a Q-TIP® brand cotton swab.

Figures 8, 9:
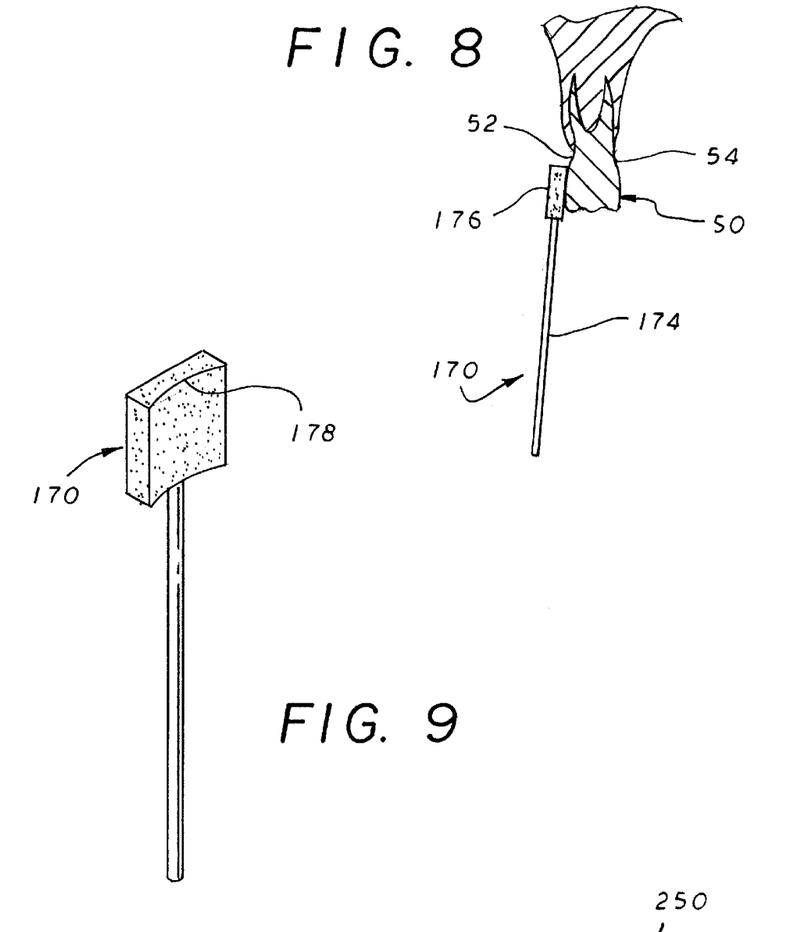
FIG. 8 shows a still further preferred embodiment of an applicator for use with the systems according to the invention.
FIG. 9 is a front perspective view of the applicator of FIG. 8.

FIGS. 8 and 9 illustrate yet another preferred embodiment of an applicator 170 according to the invention.

Applicator 170 includes a handle 174 and a material 176 disposed at one of its ends.

Material 176 may be shaped to conform to the shape of the surface of tooth 50 to enhance the application of whitening agent on tooth 50.

Material 176 may be made of a foam material, such as a cellular foam.

Applicator 170 may be disposable, in a manner similar to the other applicator embodiments.

Figure 10:
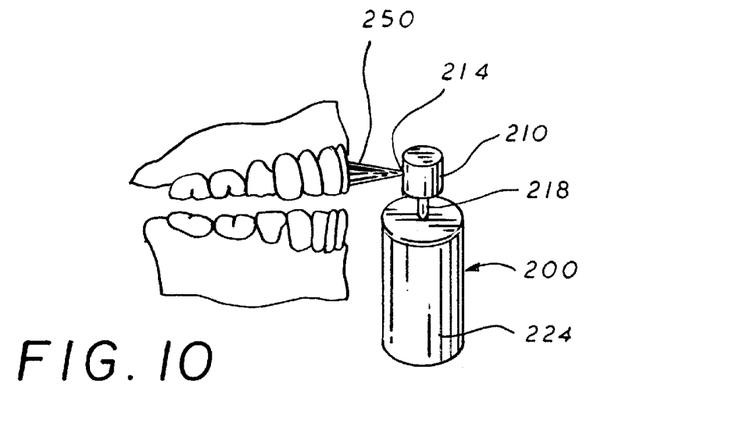
FIG. 10 illustrates yet another preferred embodiment of an applicator in the form of a sprayer in accordance with the invention.

FIG. 10 shows a still further preferred embodiment of an applicator 200 in accordance with the invention.

Applicator may include a sprayer including an actuator button 210 having a nozzle 214 therein. A fluid passage 218, such as the illustrated tube, may be used to connect nozzle 214 to a canister 224. Canister 224 may be a pressurized or pressurizable cylinder. A conventional pressurized sprayer or so-called "spray can" pre-filled with the whitening agent and carrier may be used. Such may be similar to pocket-sized pressurized breather freshener canisters that are readily available.

In use, it is contemplated that the whitening compounds described herein may be applied by hand, such as by applying the whitener to a fingertip then daubing on the whitening compound with the user's fingertip(s) or the dentist's fingertip(s).

Depending on the strength of the whitening agent, and whether or not a dentist is the one applying the whitening compound to the patient's teeth, reusable or disposable surgical gloves may be used when applying the whitening compound.

In use, the sprayer 200 of FIG. 10 will be held at a distance typically selected so that there will be little or no overspray. In other words, so that whitening compound 250 is sprayed substantially only onto the patient's teeth, as illustrated, and little, if any, of compound 250 is sprayed onto the patient's gums or tongue, for example.

It is contemplated that in any of the embodiments of FIGS. 1–10 any suitable whitening agent may be used that can whiten without irritating the mouth tissues.

In the case of the preferred embodiment of FIGS. 4–6 where overcoat 110 is used in conjunction with whitening agent 60, whitening agent 60 need not be a material selected so as to not irritate the mouth tissue. That is because overcoat 110 will be made of a material selected to protect the mouth tissue from whitening agent 60.

In a preferred embodiment of the invention, whitening agent 60 may have the following range of compositions.

Each of the following compositions may be made in a manner similar to that spelled out below in connection with Solution No. 16. For example, the solids may be dissolved in the respective ethanols, and the balance brought up to a total volume of 100 ml by adding the respective ethanols, as required, to yield 100 ml of the respective compositions.

| WHITENING AGENT COMPOSITION A1 (to yield 100 ml of composition) | |
| --- | --- |
| Undenatured Ethanol | balance ml |
| Urea Peroxide | 0.5–40 g |
| Copal | 5–20 g |
| Cetostearyl Alcohol | 1–20 g |
| total | 100 ml |

| WHITENING AGENT COMPOSITION A2 (to yield 100 ml of composition) | |
| --- | --- |
| Ethanol (ethyl alcohol) | balance ml |
| Urea Peroxide | .001–40 g |
| Resin | .001–30 g |
| Hydroxyl propyl cellulose | .001–20 g |
| total | 100 ml |

A preferred embodiment of the protective layer or overcoat 110 may have the following compositions.

| PROTECTIVE LAYER COMPOSITION B1 (total yield 100 ml of composition) | |
| --- | --- |
| Undenatured Ethanol | balance ml |
| Copal | 5–20 g |
| Cetostearyl Alcohol | 1–20 g |
| total | 100 ml |

| PROTECTIVE LAYER COMPOSITION B2 (total yield 100 ml of composition) | |
| --- | --- |
| Ethanol (ethyl alcohol) | balance ml |
| Urea Peroxide | .001–40 g |
| Resin | .001–30 g |
| Hydroxyl propyl cellulose | .001–40 g |
| total | 100 ml |

A further preferred embodiment of the whitening agent follows.

| WHITENING AGENT COMPOSITION A3 (total yield 100 ml of composition) | |
| --- | --- |
| Undenatured Ethanol | balance ml |
| Urea Peroxide | 10 g |
| Copal | 10 g |
| Cetostearyl Alcohol | 5 g |
| total | 100 ml |

| WHITENING AGENT COMPOSITION A4 (total yield 100 ml of composition) | |
| --- | --- |
| Ethanol (ethyl alcohol) | balance ml |
| Urea Peroxide | 8 g |
| Resin | 10 g |
| Hydroxyl propyl cellulose | .5 g |
| total | 100 ml |

Whitening agent 110 of composition A3 may be made with 100% pure undenatured ethyl alcohol and 98% pure urea peroxide.

Rosin may be substituted for resin in all formulas.

Urea hydrogen peroxide may be substituted for urea peroxide in all formulas.

Whitening agents requiring no protective layer may be formulated as follows:

| WHITENING AGENT COMPOSITION A5 (total yield 100 ml of composition) | |
| --- | --- |
| Rosin | .001–30 g |
| Urea hydrogen peroxide | .001–40 g |
| Hydroxypropyl cellulose 1500 cps | .001–20 g |
| Ethyl alcohol (95%) | balance ml |
| Total Volume | 100 ml |

The following is an example of a tooth whitening compound that has been formulated in accordance with the invention, and which whitening compound was of the type that did not require a protective layer.

The following is the formulation of a procedure for making 100 ml of a Solution No. 16.

In the following formula, the resin, the urea hydrogen peroxide USP, and the hydroxypropyl cellulose 1500 cps are all expressed as a weight per volume (w/v; i.e., g/100 ml) and the ethanol 95 was added in a quantity as needed (q.s.) to yield the desired 100 ml of whitening agent.

| WHITENING AGENT COMPOSITION OF SOLUTION NO. 16 (total yield 100 ml of composition) | |
| --- | --- |
| Rosin | 12.5 g |
| Urea hydrogen peroxide | 8.0 g |
| Hydroxypropyl cellulose 1500 cps | 0.5 g |
| Ethyl alcohol (95%) | balance ml |
| Total Volume | 100 ml |

Solution No. 16 was formulated as follows to yield 100 ml of product:
1. Dissolve 12.5 g of resin in 75 ml of the ethanol in a beaker having a spin bar therein;
2. The spin bar was spun using the spinning device (stirrer) of an unheated hot plate of the type having a magnetic stirrer disposed therein, the spinning was continued until the unheated rosin and ethanol solution was clear;
3. 8 g of the urea hydrogen peroxide were weighed out and ground into a fine powder using a mortar and pestle, added to the rosin and ethanol solution, and then stirred on the spinning device. A cloudy solution resulted.

4. As the rosin and ethanol solution was spinning, the 0.5 g of hydroxypropyl cellulose was added gradually (sprinkled into the vortex of the spinning solution resulting from the magnetic stir bar) in small amounts at a time. The spinning was continued for about an hour until the solution began to gel. Enough ethyl alcohol (95%) was added q.s. to bring the volume up to 100 ml, and the spinning was continued.

5. The mixed solution was put in a refrigerator (at about 40° F.) and left overnight (i.e., about 19–20 hours) to allow the solution to completely hydrolyze.

6. The refrigerated solution was removed from the refrigerator and again spun at room temperature at about 70° F.) for about 30 minutes to throughly mix the solution. The prepared solution was then put into the desired containers.

It should be noted that in Step 4 of spinning the solution having the rosin, the urea hydrogen peroxide 1500 cps, and the hydroxypropyl cellulose, the added materials may not throughly dissolve. It appears that the step of allowing the solution to sit overnight in the refrigerator for a period of time, and then remixing the solution succeeds in yielding a homogeneous solution with the added materials dissolved and dispersed throughout.

The following is the formulation of a Solution No. 18 that has been made.

| WHITENING AGENT COMPOSITION OF SOLUTION NO. 18 (total yield 60 ml (i.e., 51.43 g) of composition) | |
|---|---|
| Rosin | 7.5 g |
| Urea hydrogen peroxide | 3.6 g |
| Hydroxypropyl cellulose 1500 cps | 0.3 g |
| Ethyl alcohol (95%) | 40.0 g |
| Spearmint Extract (1 drop) | 0.03 g |
| Total Weight | 51.43 g |

Thus, Solution No. 18 can be expressed on a weight per weight (w/w) basis of about 14.6% rosin; 7.0% urea hydrogen peroxide; 0.6% hydroxypropyl cellulose 1500 cps; 77.8% ethyl alcohol; and 0.06% spearmint extract; the total is not exactly 100% owing to the rounding of the percentages to one(1) significant digit.

Solution No. 18 was prepared in a manner analogous to that as described above in connection with the preparation of Solution No. 16.

It will be seen that the achievement of a tooth whitening delivery system has been realized that provides for directly applying a whitening agent onto the surfaces of the teeth, thus eliminating the need for any type of tray or other type of carrier.

In other words, the invention achieves the object of an elegantly simple solution to the problem of expensive laborious and unwieldy tooth whitening systems that made such unavailable to the vast majority of the patient population.

The tooth whitening system achieves the goal of applying and retaining a whitening agent against the patient's teeth without the need for a mouth tray or other retaining wall or retaining means that had previously been necessary.

The method may be carried out without the use of a mouth tray, mold, or other retaining wall for keeping the whitening agent in place against the teeth. Such trays have previously been required to protect the soft mouth tissue as well.

The whitening compound in one basic form includes a combined carrier that adheres to the patient's teeth, and a whitening agent.

The inventive method eliminates the traditional use of any form of mouth trays for teeth whitening.

The invention further includes a teeth whitener having a novel carrier that temporarily adheres to the tooth for the purpose of whitening the tooth with or without a desensitizing agent.

The tooth whitener is bound in the resin and is released or is activated by moisture or water from the mouth (i.e., from the saliva in the mouth) rather than by the tooth structure itself. It is believed that owing to the whitening compound being released throughout the thickness of the applied resin, the active layer is against the tooth being whitened, which tooth is buried in the resin. The hydrogen peroxide or peroxide compound against the mouth tissue is neutralized or broken down by the water in the saliva. In that manner, the tissue is unharmed.

It has been observed that the whitening compound is released (activated throughout the resin for a period of about or about 10–30 minutes). This is seen as an effervescing over the coated tooth surfaces. This can be easily removed by brushing; and additional application(s) of the whitening compounds may be applied. It may be that the whitening compound is activated (released) against the tooth surfaces for a much longer time than the time period during which the effervescence is observed.

The following formulations are in accordance with the invention.

A whitening compound suitable for applying to teeth may comprise by weight percent:

| | |
|---|---|
| a) Undenatured Ethanol | 40–80%; |
| b) Urea Peroxide | 0.5–40%; |
| c) Copal | 5–20%; and |
| d) Cetostearyl Alcohol | 1–20%. |

A whitening agent may include by weight percent:

| | |
|---|---|
| Undenatured Ethanol | 75%; |
| Urea Peroxide | 10%; |
| Copal | 10%; and |
| Cetostearyl Alcohol | 5%. |

An overcoat for being applied to a tooth whitening compound, the overcoat may comprise by weight percent:

| | |
|---|---|
| a) Undenatured Ethanol | 40–80% |
| b) Copal | 0.5–20%; and |
| c) Cetostearyl Alcohol | 1–20% |

A whitening compound may comprise in weight percent:
a) the rosin is about 0.001–30%;
b) the urea hydrogen peroxide is about 0.001–40%;
c) the hydroxypropyl cellulose is about 0.001–20; and
d) the balance is ethyl alcohol.

The inventive method also comprises a novel active ingredient imbedded in or carried by a novel carrier that permits sustainable release of the active ingredient and that would be painted on or brushed on the tooth surface and would remain active for a period of time.

The carrier may be the copal described above or another non-toxic adhesive or resin. The copal may be copal varnish supplied by Cooley & Cooley of Houston, Tex. The adhesive or resin may be synthetic or natural. The resin may be a rosin.

The rosin may be a refined hydrogenated rosin such as supplied by Cooley & Cooley of Houston, Tex.; e.g., Lot No. 00040702-3, as described above.

The whitening agent may be any peroxide derivative or other chemical component that would whiten teeth. The whitening agent may be provided in varying concentrations depending on the carrier in which the agent is provided, as well as depending on the degree of whitening required, the physical properties of the teeth, and the like. For example, urea hydrogen peroxide, C.A.S. No. 124-43-6, supplied by Professional Compounding Centers of America of Houston, Tex. may be used as described above.

Other known peroxides may be substituted for the above-described peroxides.

Sodium bicarbonate may be substituted for peroxide(s) as the whitening agent.

It is contemplated that the whitening compound will be selected so that the whitening agent and the carrier will yield a release of the whitening agent to the tooth surface over time. This optional time-release mechanism may be for less than a few minutes to ten(10) hours or more.

The hydroxypropyl cellulose may be as supplied by Professional Compounding Centers of America, Houston, Tex.; e.g., hydroxypropyl cellulose 1500 cps, C.A.S. No. 9004-64-2, part no. 30-1996-100, Lot No. 26855, obtained in a 100 g lot, and used as described above.

The spearmint oil may be Spearmint Oil N.F (i.e., National Formulary), supplied by Professional Compounding Centers of America (P.C.C.A.), Houston, Tex., Part No. 30-1178-30 used as described above.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

What is claimed is:

1. A method of whitening teeth, comprising:
   a) providing a whitening compound, the whitening compound including a resin, the resin causing the whitening compound to adhere to a patient's tooth; and
   b) painting the whitening compound on a patient's tooth.
2. A method as in claim 1, wherein:
   a) said step of painting the whitening compound is performed by brushing the whitening compound on a surface of the patient's tooth.
3. A method as in claim 1, wherein:
   a) said step of painting the whitening compound is performed by sponging the whitening compound on a surface of the patient's tooth.
4. A method as in claim 1, wherein:
   a) said step of painting the whitening compound is performed by daubing the whitening compound on a surface of the patient's tooth.
5. A method as in claim 1, wherein:
   a) said step of painting the whitening compound is performed by applying the whitening compound directly on a surface of the patient's tooth.
6. A method as in claim 1, wherein:
   a) said step of painting the whitening compound is performed by spraying the whitening compound on a surface of the patient's tooth.
7. A method as in claim 1, wherein:
   a) after said step of painting on the whitening compound the applied whitening compound remains uncovered.
8. A method as in claim 1, wherein:
   a) the whitening compound includes a carrier and a whitening agent.
9. A method as in claim 8, wherein:
   a) the carrier includes an adhesive.
10. A method as in claim 9, wherein:
    a) the adhesive is a non-toxic adhesive.
11. A method as in claim 10, wherein:
    a) the adhesive is a synthetic adhesive.
12. A method as in claim 9, wherein:
    a) the adhesive is a natural adhesive.
13. A method as in claim 1, wherein:
    a) the resin is a non-toxic resin.
14. A method as in claim 1, wherein:
    a) the resin is a synthetic resin.
15. A method as in claim 1, wherein:
    a) the resin is a natural resin.
16. A method as in claim 1, wherein:
    a) the whitening compound includes a whitening agent.
17. A method as in claim 16, wherein:
    a) said whitening agent includes urea hydrogen peroxide.
18. A method as in claim 16, wherein:
    a) said whitening agent includes a peroxide derivative.
19. A method as in claim 16, wherein:
    a) said whitening agent includes urea peroxide.
20. A method as in claim 16, wherein:
    a) said whitening agent includes sodium bicarbonate.
21. A method as in claim 1, wherein:
    a) the whitening compound includes:
       i) a carrier;
       ii) a whitening agent compound; and
       iii) the whitening agent compound includes an active whitening agent which is activatable by water from a tooth to which the whitening compound is to be applied.
22. A method as in claim 21, wherein:
    a) the whitening agent is activatable by saliva.
23. A method as in claim 21, wherein:
    a) the carrier includes an adhesive.
24. A method as in claim 23, wherein:
    a) the adhesive is a non-toxic adhesive.
25. A method as in claim 23, wherein:
    a) the adhesive is a synthetic adhesive.
26. A method as in claim 23, wherein:
    a) the adhesive is a natural adhesive.
27. A method as in claim 21, wherein:
    a) the whitening agent includes a time-release whitening agent.
28. A method as in claim 21, wherein:
    a) said whitening agent includes a peroxide.
29. A method as in claim 21, wherein:
    a) said whitening agent includes a peroxide derivative.
30. A method as in claim 21, wherein:
    a) said whitening agent includes urea peroxide.
31. A method as in claim 21, wherein:
    a) said carrier is selected so as to adhere to a human tooth.
32. A method as in claim 31, wherein:
    a) said carrier adheres sufficiently long without the aid of a retaining device that the whitening agent therein can whiten human tooth.

33. A method as in claim 31, wherein:
a) said carrier adheres sufficiently long without the aid of a mouth tray that the whitening agent therein can whiten a human tooth.

34. A method as in claim 31, wherein:
a) said carrier adheres sufficiently long without the aid of a tape that the whitening agent therein can whiten a human tooth.

35. A method as in claim 1, wherein:
a) the resin includes a natural resin.

36. A method as in claim 35, wherein:
a) said natural resin includes copal.

37. A method as in claim 35, wherein:
a) said natural resin includes copal varnish.

38. A method as in claim 1, wherein:
a) said step of painting on the whitening compound is performed without the use of an external support.

39. A method as in claim 1, wherein:
a) said step of painting on the whitening compound is performed without the use of a mouth tray.

40. A method of whitening teeth, comprising:
a) providing a whitening compound, the whitening compound including a resin, the resin causing the whitening compound to adhere to a patient's tooth; and
b) applying the whitening compound on a patient's tooth in an uncovered layer.

41. A method as in claim 40, wherein:
a) said step of applying the whitening compound is performed by brushing the whitening compound on a surface of the patient's tooth.

42. A method as in claim 40, wherein:
a) said step of applying the whitening compound is performed by sponging the whitening compound on a surface of the patient's tooth.

43. A method as in claim 40, wherein:
a) said step of applying the whitening compound is performed by painting the whitening compound on a surface of the patient's tooth.

44. A method as in claim 40, wherein:
a) said step of painting the whitening compound is performed by applying the whitening compound directly on a surface of the patient's tooth.

45. A method as in claim 43, wherein:
a) after said step of painting on the whitening is compound the applied whitening compound remains uncovered.

46. A method as in claim 40, wherein:
a) said step of applying the whitening compound is performed by daubing the whitening compound on a surface of the patient's tooth.

47. A whitening compound suitable for applying to teeth, said whitening compound comprising, by weight percent:

| | |
|---|---|
| a) Undenatured Ethanol | 40–80%; |
| b) Urea Peroxide | 0.5–40%; |
| c) Copal | 5–20%; and |
| d) Cetostearyl Alcohol | 1–20%. |

48. A whitening compound as in claim 47, wherein said whitening compound includes, by weight percent:

| | |
|---|---|
| Undenatured Ethanol | 75%; |
| Urea Peroxide | 10%; |
| Copal | 10%; and |
| Cetostearyl Alcohol | 5%. |

49. An overcoat for being applied to a tooth whitening compound, said overcoat comprising by weight percent:

| | |
|---|---|
| a) Undenatured Ethanol | 40–80% |
| b) Copal | 0.5–20%; and |
| c) Cetostearyl Alcohol | 1–20% |

50. A whitening compound suitable for applying to teeth, comprising:
a) rosin;
b) urea hydrogen peroxide;
c) hydroxypropyl cellulose; and
d) ethyl alcohol.

51. A compound as in claim 50, wherein:
a) said hydroxypropyl cellulose includes hydroxypropyl cellulose 1500 cps.

52. A compound as in claim 51, wherein:
a) said ethyl alcohol includes 95% ethyl alcohol.

53. A compound as in claim 50, wherein:
a) said ethyl alcohol includes 95% ethyl alcohol.

54. A compound as in claim 39, wherein, in weight percent,
a) the rosin is about 0.001–30%;
b) the urea hydrogen peroxide is about 0.001–40%;
c) the hydroxypropyl cellulose is about 0.001–20; and
d) the balance is ethyl alcohol.

55. A compound as in claim 54, wherein, in weight percent,
a) the rosin is about 12.5%;
b) the urea hydrogen peroxide is about 8%;
c) the hydroxypropyl cellulose is about 0.5%; and
d) the balance is ethyl alcohol.

56. A method of whitening teeth, comprising:
a) providing a whitening compound, the whitening compound including an adhesive which adheres to the tooth of a patient without the use of a thermally responsive viscosity modifier of the type which increases viscosity of the adhesive responsive to an increase in temperature; and
b) painting the whitening compound on a patient's tooth.

57. A method as in claim 56, wherein:
a) said step of painting the whitening compound is performed by brushing the whitening compound on a surface of the patient's tooth.

58. A method as in claim 56, wherein:
a) said step of painting the whitening compound is performed by sponging the whitening compound on a surface of the patient's tooth.

59. A method as in claim 56, wherein:
a) said step of painting the whitening compound is performed by daubing the whitening compound on a surface of the patient's tooth.

60. A method as in claim 56, wherein:
a) said step of painting the whitening compound is performed by painting the whitening compound directly on a surface of the patient's tooth.

61. A method as in claim 56, wherein:
a) said step of painting the whitening compound is performed by spraying the whitening compound on a surface of the patient's tooth.

62. A method as in claim 56, wherein:
a) after said step of painting on the whitening compound the applied whitening compound remains uncovered.

63. A method as in claim 56, wherein:
a) the adhesive is a non-toxic adhesive.

64. A method as in claim 56, wherein:
a) the adhesive is a synthetic adhesive.

65. A method as in claim 56, wherein:
a) the adhesive is a natural adhesive.

66. A method as in claim 56, wherein:
a) the whitening compound includes a carrier.

67. A method as in claim 66, wherein:
a) the carrier includes a resin.

68. A method as in claim 67, wherein:
a) the resin is a synthetic resin.

* * * * *